(12) United States Patent
Hermitte et al.

(10) Patent No.: US 8,052,990 B2
(45) Date of Patent: Nov. 8, 2011

(54) BIOCOMPATIBLE CROSSLINKED GEL

(75) Inventors: Laurence Hermitte, Luynes (FR); Olivier Benoit, Annecy (FR)

(73) Assignee: Anteis S.A., Plan-les-Ouates, Geneva (CH)

( * ) Notice: Subject to any disclaimer, the term of this patent is extended or adjusted under 35 U.S.C. 154(b) by 865 days.

(21) Appl. No.: 10/588,186

(22) PCT Filed: Jan. 31, 2005

(86) PCT No.: PCT/FR2005/000197
§ 371 (c)(1), (2), (4) Date: Aug. 2, 2006

(87) PCT Pub. No.: WO2005/085329
PCT Pub. Date: Sep. 15, 2005

(65) Prior Publication Data
US 2007/0196426 A1   Aug. 23, 2007

(30) Foreign Application Priority Data
Feb. 3, 2004   (FR) ..................... 04 00987

(51) Int. Cl.
*A61F 2/02* (2006.01)

(52) U.S. Cl. ........ 424/426; 514/772; 514/781; 514/782; 525/54.1; 525/54.2

(58) Field of Classification Search .................. None
See application file for complete search history.

(56) References Cited

U.S. PATENT DOCUMENTS

| 5,827,937 | A | * | 10/1998 | Ågerup | ................... 536/123.12 |
| 6,060,582 | A | * | 5/2000 | Hubbell et al. | ............... 528/354 |
| 6,165,489 | A | * | 12/2000 | Berg et al. | ..................... 424/426 |
| 6,174,999 | B1 | * | 1/2001 | Miller et al. | .................... 536/21 |
| 2002/0049281 | A1 | * | 4/2002 | Zhao et al. | ................... 525/54.3 |
| 2003/0232198 | A1 | * | 12/2003 | Lamberti et al. | ........... 428/423.1 |

FOREIGN PATENT DOCUMENTS

| EP | 0 161 887 | 11/1985 |
| WO | 96/33751 | 10/1996 |
| WO | 97/04012 | 2/1997 |
| WO | 02/06350 | 1/2002 |

\* cited by examiner

*Primary Examiner* — Carlos Azpuru
*Assistant Examiner* — David M Browe
(74) *Attorney, Agent, or Firm* — Young & Thompson

(57) ABSTRACT

The invention relates to a method for producing a biocompatible crosslinked gel consisting in crosslinking a determined quantity of at least one type of liquid biocompatible polymer by adding a quantity of crosslinking agent, in carrying out a crosslinking reaction, in adding an additional quantity of liquid polymer whose molecular mass is greater than 500,000 Da, in solving the reaction mixture in such a way that the total concentration of the liquid polymer is reduced, in crosslinking and in stopping the crosslinking reaction by removing the crosslinking agent. The inventive gel and the use thereof are also disclosed.

23 Claims, No Drawings

BIOCOMPATIBLE CROSSLINKED GEL

The present invention relates to a process for the production of a biocompatible crosslinked gel, said gel and the use of said gel to constitute a matrix comprising at least one dispersed active principle or to separate, replace or fill a biological tissue or to increase the volume of said tissue or else to supplement or replace a biological fluid.

The increase of tissue volume can be desired both in the case of therapeutic applications and for cosmetic purposes. It can be carried out by introduction of a viscoelastic solution based on permanent or biodegradable products into the biological tissues.

The injection of viscoelastic solutions based on permanent or biodegradable products is also envisaged to replace a biological fluid.

For example, it is used to replace the natural synovial liquid which, in arthritic patients, can no longer fulfill the chondroprotective functions, of lubrication and absorption of shocks given a reduction in quantity and molecular weight of the constituent glycosaminoglycanes. But this viscoelastic solution, when it is constituted by biodegradable products, is rapidly eliminated from the synovial pocket.

In the case of other therapeutic applications, this type of viscoelastic solution is used for certain tissues which require being enlarged to ensure their function; the examples are vocal cords, the esophagus, the sphincter or the urethra.

In the case of cosmetic applications, this type of viscoelastic solution is used for example for filling wrinkles, masking scars, or increasing the volume of the lips. The injection of these viscoelastic solutions is a simple non-evasive method, with less risk and less trouble than aesthetic surgery.

The use of viscoelastic solutions based on permanent products has the advantage of long persistence in the tissues where the viscoelastic solution is injected.

The injection of silicone has been used for a long time. However, given the undesirable long term effects of this method, which is characterized by the appearance of nodules and ulcers of the skin, this practice is being gradually abandoned.

The injection of microparticular solids in suspension also permits a permanent increase in the tissue volume. U.S. Pat. No. 5,344,452 discloses the use of a pulverulent solid, constituted by small particles, of a diameter comprised between 10 μm and 200 μm, and having a very smooth surface. ARTECOLL® and ARTEPLAST®, commercial products, are constituted by a suspension of microspheres of polymethacrylate in a solution of collagen. The patent EP 091 775 proposes a suspension of fragments of methacrylate hydrogel in a solution of hyaluronate. The particles of silicone, ceramics, of carbon or metals (U.S. Pat. Nos. 5,451,406, 5,792,478 and U.S. application 2002-151466), and the fragments of polytetrafluoroethylene, of glass or of synthetic polymers (U.S. application 2002-025340) have also been used but the results are disappointing. Thus, secondary reactions, issues of biological degradation of the solution or biodegradable suspension and migration of residual fragments that can induce an inflammatory reaction, can appear. Moreover, the injection of particles through a fine needle can be difficult if the particles have too great a diameter or an irregular shape which can give rise to agglomeration of the particles with each other. Moreover, the injection of fragile particles can damage their structure which leads to injection of too small particles which do not adhere to the neighboring cells but migrate toward other tissues or are rapidly digested by macrophages and the other constituents of the lymphatic system.

Generally speaking, the permanent character of these products leads to major drawbacks (U.S. Pat. No. 6,436,424) which have notably the risk of actuation of macrophages, the migration of synthetic fragments constituting the product being able to give rise to an inflammatory action that can even lead to the appearance of granulomas. The treatment of these granulomas thus requires either a therapeutic treatment by injection of steroids or a surgical treatment by excision, these treatments being able to have severe consequences on the health of the patient or his quality of life. As a result, the secondary effects of the permanent products are so troublesome that they discourage the use of these products for purely aesthetic purposes. Moreover, the injection of a viscoelastic solution based on permanent products does not permit retouching if needed.

Among the biologically degradable materials, there are suspension of collagen or of cross-linked hyaluronic acid.

Collagen Corporation has developed a preparation based on collagen crosslinked with glutaraldehyde disclosed in U.S. Pat. No. 4,582,640. However, this product is rapidly degraded in the tissue in which it is injected, by macrophages, or by enzymatic or chemical action, and is then eliminated from the tissue by the lymphatic system. U.S. Pat. No. 5,137,875 proposes the use of suspensions or aqueous solutions of collagen containing hyaluronic acid, but this product cannot constitute a long-term treatment because it is also rapidly digested and then eliminated by the lymphatic system. Repeated treatments are thus necessary, which gives rise to considerable cost and decreases the quality of life of the patient.

The patent EP 0 466 300 proposes the injection of a biphasic viscoelastic gel comprised of a matrix dispersed in a liquid phase, the two phases being comprised by hyalan, hyaluronate of high molecular weight of animal origin, crosslinked and extracted. The use of a polymer of high molecular weight permits a longer persistence of the biodegradable viscoelastic gel in the tissue. This technology has given rise to several products on the market, such as HYLAFORM®, for filling depressions of the intercellular matrix of the conjunctive tissue, or SYNVISC®, product of viscosupplementation for the treatment of arthritis.

Among the biphasic biodegradable products, can also be cited RESTYLANE®, MACROLANE®, PELANE®, or DUROLANE®, other biphasic compositions constituted by a fluid phase (non-crosslinked hyaluronate) and a phase comprised by highly crosslinked hyaluronic acid. Adapted for the increase of the tissue volume (face, breast) or the treatment of arthritis, these products are based on the NASHA technology owned by Q-Med. It has also been observed that, under certain circumstances, the use of biphasic products can induce inflammatory reactions or even give rise to the appearance of granulomas (Laeschke K. Biocompatibility of microparticles into soft tissues fillers. Congress of Aesthetic Medicine and Dermatologic Surgery, Paris, 2003) even if these reactions are less observed than the presence of a gel based on synthetic polymers. Moreover, the fluid phase is very rapidly eliminated, which gives rise to a loss of material corresponding to the volume of this fluid phase. As a result, when increase in the volume of the tissue is sought, numerous retouches are necessary after the first injection, which decreases the quality of life of the user.

Finally, several monophasic viscoelastic gels have been proposed either for homogenizing the quantity of crosslinking in the gel (U.S. Patent Application 2003-148995), or to control the biodegradability of the gel (U.S. Pat. No. 4,963,666), or to control viscoelastic properties of the gel (U.S. Pat. No. 5,827,937). A high degree of crosslinkage of the polymers permits greater persistence in the tissue of the biodegradable viscoelastic gel. However, the injection of the gel comprising such a highly crosslinked polymer is more difficult. Moreover, the injection of such a gel renders mechanically fragile the non-crosslinked sites of the polymer which become more vulnerable to biochemical and enzymatic attacks, which promotes rapid degradation of the gel.

The invention has for its object to propose a biocompatible crosslinked gel which avoids the mentioned drawbacks, which has the advantages simultaneously of easy use in its clinical utilization and of a lifetime such that the biocompatible crosslinked gel disappears when its function is no longer desired, but sufficient to limit the number of administrations by medical or surgical intervention.

To this end, the invention has for its object a process for the production of a biocompatible crosslinked gel, comprising the steps:

of beginning crosslinkage of a predetermined quantity of at least one biocompatible polymer in solution by the addition of a quantity of crosslinking agent, of the crosslinking reaction of said quantity of polymer, of adding a supplemental quantity of polymer of a molecular weight higher than 500,000 Da in solution with dilution of the reaction mixture so as to decrease the overall concentration of the polymer in solution, and crosslinking, and stopping the crosslinking reaction by elimination of the crosslinking agent.

The step of adding a supplemental quantity of polymer permits providing new reaction sites.

This process permits obtaining a biocompatible crosslinked gel having simultaneously the characteristics of being monophasic, polydensified, cohesive, injectable and with long persistence.

By cohesive, there is meant a tendency of the gel to regroup and not to spread out or break apart. The cohesive character thus contributes to obtaining a high compatibility and long persistence in vivo of the gel.

By polydensification, there is meant a variation of the degree of crosslinking even within the gel itself. The polydensified character of the gel permits the composition to acquire advantages of injectability through a needle of small diameter, and all persistence in vivo of the gel.

The monophasic character permits reducing the risk of inflammatory reactions and the appearance of granulomas.

The effect of long persistence of the gel permits spacing the medical interventions and hence improving the quality of life of the patients.

Such a cohesive polydensified monophasic gel obtained according to the practice of the present invention is characterized by facilitated injectability and persistence in vivo longer than that of a monophasic gel of the same composition, whose amount of crosslinking is homogeneous within the gel.

According to a particular embodiment of the invention, the step of beginning crosslinking is carried out in a basic medium.

According to another embodiment of the invention, the step of beginning crosslinking is carried out in an acid medium.

According to a modification of the invention, a supplemental quantity of crosslinking agent is added during the step of addition of a supplemental quantity of polymer.

Preferably, the step of stopping crosslinking is carried out by dialysis. The dialysis ensures the final stopping of the reaction. It eliminates the crosslinking agent and the small polymer chains that have not reacted.

Desirably, the polymers are of natural origin. The use of polymer of natural origin permits better biocompatibility, which is to say that such a use give rise to less risk of inflammatory reaction.

Preferably, the polymer of natural origin are compounds selected from the group consisting of: hyaluronic acid, chondrotin sulfate, keratan, keratan sulfate, heparin, heparin sulfate, cellulose and its derivatives, alginates, xanthane, carrageenan, proteins or nucleic acids.

Even more desirably, at least one polymer of natural origin is a polymer not naturally present in the human body, selected from the group consisting of: cellulose and its derivatives, alginates, xanthane, carrageenan, a polymer which is crosslinked with at least one polymer naturally present in the human body selected from the group consisting of: hyaluronic acid, chondrotin sulfate, keratan, keratan sulfate, heparin, heparin sulfate, proteins or nucleic acids.

Desirably, the crosslinking agent is a biopolyfunctional molecule selected from compounds of the group consisting of epoxids, epihalohydrins and divinylsulfone.

The invention also has for its object a gel prepared by the above-mentioned process.

Preferably, the gel constitutes a matrix comprising at least one dispersed active principal. The gel will then be used as a vector permitting progressive release of said active principal from the liquid or the biological tissue in which it is injected.

Finally, the invention has for its object the use of this gel to separate, replace or fill a biological tissue or to increase the volume of said tissue or else to supplement or replace a biological fluid.

The invention will be better understood, and other objects, details, characteristics and advantages from the latter will become more clearly apparent, in the course of the detailed explanatory description which will follow, of an embodiment of the invention given by way purely of illustrative example and not limiting.

The process for production of the biocompatible crosslinked gel is characterized by the successive steps of beginning crosslinking of a predetermined quantity of at least one biocompatible polymer in solution, of crosslinking said quantity of polymer, of adding a supplemental quantity of polymer of a molecular weight greater than 500,000 Da in solution with dilution of the reaction mixture so as to decrease the overall concentration of the polymer in solution, of crosslinking, and of stopping the crosslinking reaction by elimination of the reticulating agent.

The start of starting crosslinking is carried out by the addition of a quantity of crosslinking agent which is a bi- or polyfunctional molecule selected from the compounds of the group consisting of epoxids, epihalohydrins and divinylsulfone. The preferred epoxids are compounds selected from the group consisting of: 1,4 butanediol diglycidyl ether (also called 1,4-bis (2,3-epoxypropoxy)butane), 1-(2,3-epoxypropyl) 2,3-epoxy cyclohexane and 1,2-ethanediol diglycidyl ether.

According to a particular embodiment of the invention, the step of starting crosslinking is carried out in a basic medium. The crosslinking reaction carried out in basic medium is characterized by the formation of ether bonds which are very solid. The crosslinking by etherification permits a longer persistence in vivo.

According to another embodiment of the invention, the step of beginning crosslinking is carried out in an acid medium. The crosslinking reaction carried out in acid medium is characterized by the formation of ester linkages which are more unstable than the ether linkages mentioned above. However, the greater unstability of the bridges can have certain advantages. Particularly, such a gel used as a matrix comprising a dispersed active principal permits another kinetic of release of said active principal more suitable for certain applications.

The crosslinking reaction is the reaction which ensures the bridging of the chains of each polymer with each other. It can be quantified by the determination of the amount of crosslinking.

The amount of crosslinking is defined as the ratio between the number of moles of crosslinking agent ensuring the bridging of the chains of each polymer, and the number of moles of the polymer units.

The crosslinking takes place in a range of temperatures preferably from 25° C. to 60° C.

The crosslinking can take place with a single polymer or with a mixture of polymers.

The polymers taking part in the crosslinking reaction can be synthetic but are preferably of natural origin. The use of polymers of natural origin permits better biocompatibility, which is to say that such use gives rise to less risk of inflammatory reaction.

Preferably, there are used the above-mentioned polymers of natural origin.

It is however obvious that the invention is not limited to the above-mentioned polymers but can use polymers of different type and size.

The step of adding a supplemental quantity of polymer is accompanied with the dilution of the reaction medium such that the overall concentration of polymer in the solution decreases.

Under these conditions, the polymer chains have new crosslinking sites which will react with the residual crosslinkage agent and/or the crosslinkage agent added in small quantity, by fixing on the initial crosslinked gel and between them with a lesser quantity of crosslinkage because the quantity of crosslinkage agent has decreased. The number of bridges on the chains of gel formed in the first step of crosslinking is greater than the number of bridges between the latter and the added chains and than the number of bridges between the added chains. The degree of crosslinking thus varies in the final gel which is constituted by strongly crosslinked hubs (for example with a quantity of crosslinkage of 25%) interconnected by a gel which is less and less crosslinked (whose quantity of crosslinkage decreases progressively and can reach 1%). This particularity gives to it exceptional viscoelastic properties which permit the gel, whilst having a large amount of crosslinkage and hence a long persistence in vivo, to be cohesive (a single and same gel) and injectable by any sort of medical devices in particular the thin needles.

The addition of supplemental polymers takes place at any level of progress of the initial crosslinkage reaction, preferably at 75% of the initial crosslinkage reaction. This step can be carried out by the addition of polymer in a continuous or discontinuous manner.

The supplemental polymers must have a molecular weight greater than 500,000 Da. They can also be synthetic or natural. They can be added in the form of a mixture of polymers. They can be of a nature or size identical to or different from those used in the initial crosslinkage step. Desirably, the added supplemental polymers are constituted by longer chains than the polymers initially present. This gives to the gel an improvement of its external mechanical structure, the long chains being more difficulty degraded than the short ones.

This process accordingly permits obtaining a biocompatible crosslinked gel having simultaneously the characteristics of being monophasic, polydensified, cohesive, injectable and with long persistence.

According to a particular embodiment of the invention, a supplemental quantity of crosslinking agent is added during the step of adding a supplemental quantity of polymer. This crosslinking agent can be of a nature identical to or different from that of the one used during the beginning of the reaction. It is preferably selected from components of the above-mentioned group. The added quantity is substantially less than the quantity added for initial crosslinkage.

The step of stopping the crosslinking reaction ensures the final stopping of the reaction. It is for example carried out by dialysis which permits eliminating the crosslinking agent and the short chains of polymer that have not reacted. Thus the injection of a gel comprising such an agent leads to inflammatory reactions because these agents are of difficulty assimilable chemical compounds and are very reactive.

Preferably, the gel constitutes a matrix comprising at least one dispersed active principal. The gel is thus used as a vector permitting progressive release of said active principal into the liquid or the biological tissue where it has been injected. The active principal is a pharmacologically active agent that can for example be an antioxidant agent. The active principal can also be of a different nature. A mixture of active principals of different nature can also be dispersed in the gel.

This gel is preferably injected.

Finally, the gel is desirably used to separate, replace or fill a biological tissue or to increase the volume of said tissue for example in the case of therapeutic applications (increase in the volume of the vocal cords, of the esophagus, of the sphincter, of the urethra or other organs) or for cosmetic purposes for the filling of wrinkles, the masking of scars, or the increase of the volume of the lips.

It can also supplement or replace a biological fluid, for example the natural synovial liquid.

Examples are proposed so as to illustrate the invention but are in no way limiting of the invention.

EXAMPLE 1

Comparative 10 g of hyaluronic acid (MW=$2\times10^6$ Da) are diluted in 100 ml of a solution of NaOH at 1%. The hyaluronic acid is hydrated by this step preliminary to crosslinkage.

The whole is homogenized in a mixture until a transparent solution is obtained.

The crosslinking reaction is then triggered by the addition of 470 µl of 1,4-butanediol diglycidyl ether (BDDE) to the solution and the whole is mixed for 15 h at 25° C., in an oxygen free atmosphere.

The pH is readjusted to the physiological pH with HCl 1M. The volume is adjusted to 400 ml with the help of a buffered solution at pH=7.

The obtained gel is then dialyzed for 24 h (regenerated cellulose, limit of separation: MW=60 kDa) against a buffered solution at pH=7 (Gel I).

This gel has a total hyaluronic acid content of 2.5% by weight.

EXAMPLE 2

Comparative

The gel is made in the same way as in Example 1 except that a greater quantity of crosslinking agent is added.

10 g of hyaluronic acid (MW=2×10⁶ Da) is diluted in 100 ml of a 1% solution of NaOH.

The whole is homogenized in a mixture until a transparent solution is obtained.

760 µl of 1,4-butanediol diglycidyl ether (BDDE) is then added to the solution and the whole is mixed for 15 h at 25° C., in an oxygen free atmosphere.

The pH is readjusted to the physiological pH with 1M HCl.

The volume is adjusted to 400 ml with a buffered solution at pH=7.

The obtained gel is then dialyzed for 24 h (regenerated cellulose, limit of separation: MW=60 kDa) against a buffered solution at pH=7 (Gel II).

This gel has a total hyaluronic acid content of 2.5% by weight.

EXAMPLE 3

Comparative

The gel is made in the same way as in Examples 1 or 2, except that an even greater quantity of crosslinking agent is added.

10 g of hyaluronic acid (MW=2×10⁶ Da) is diluted in 100 ml of a 1% NaOH solution.

The whole is homogenized in a mixture until a transparent solution is obtained.

950 µl of 1,4-butanediol diglycidal ether (BDDE) is then added to the solution and the whole is mixed for 15 h at 25° C., in an oxygen free atmosphere.

The pH is readjusted to physiological pH with 1M HCl.

The volume is adjusted to 400 ml with a buffered solution at pH=7 and the whole is homogenized.

The obtained gel is then dialyzed for 24 h (regenerated cellulose, limit of separation: MW=60 kDa) against a buffered solution at pH=7 (Gel III).

This gel has a total hyaluronic acid content of 2.5% by weight.

EXAMPLE 4

According to the Invention 10 g of hyaluronic acid (MW=2×10⁶ Da) is diluted in 100 ml of a 1% NaOH solution.

The whole is homogenized in a mixture until a transparent solution is obtained.

The crosslinking reaction is triggered by the addition of 950 µl of 1,4-butanediol diglycidal ether (BDDE) and the whole is mixed for 9 h at 25° C., in an oxygen free atmosphere.

Then a supplemental polymer is added whilst adjusting the volume to 300 ml with a 0.5% hyaluronic acid solution, pH=11 (MW=2×10⁶ Da).

The reaction continues a further 6 h. The pH is readjusted to physiological pH with 1M HCl and the volume is adjusted to 400 ml.

The whole is homogenized.

So as to stop finally the crosslinking reaction, the obtained gel is then dialyzed for 24 h (regenerated cellulose, limit of separation: MW=60 kDa) against a buffered solution at pH=7 (Gel IV).

Only this latter gel is produced according to the invention, the three other types of gel being produced according to the prior art, which his to say with uniform crosslinkage.

This gel has a total hyaluronic acid content of 2.75% by weight.

A rheological study was carried out on the gels of Examples 1 to 4.

This study consisted in the measurement of the limit force of extrusion (F) of a gel, which is to say the force from which the gel can be extruded.

To do this, the gel is contained in a stainless steel cylinder 2.5 cm in diameter and extruded through a pore 0.2 mm in diameter.

The results obtained are given in the following table:

| Type of gel | $F (N/mm^2) \sigma = 0.15 N/mm^2$ |
|---|---|
| I | 3.56 |
| II | 5.85 |
| III | 7.40 |
| IV | 6.12 |

σ: typical variation

Gels I, II and III are gels whose quantity of crosslinkage is constant throughout the gel. Only gel IV is a gel whose quantity of crosslinkage is variable.

This method shows first of all that an increasing addition of crosslinking agent (from gels of type I to III) results in a limit force of extrusion that is also greater, which is to say that the force to be applied to extrude a gel with an increasing amount of crosslinkage, increases for gels having a homogenous quantity of crosslinkage.

The gel of type IV (gel according to the invention) with 2.75% by weight of hyaluronic acid injects about as easily as a gel with 2.5% by weight of hyaluronic acid with a lesser quantity of crosslinkage and which is homogenous (gel with type II) and more easily (with a force F 15% less) than a gel with 2.5% by weight of hyaluronic acid whose amount of crosslinkage is identical but homogenous (gel of type III).

As a result, this example proves that a gel according to the invention, whose amount of crosslinkage is heterogeneous, permits, with a high degree of crosslinkage, and hence with high persistence in vivo, to be easily extruded by devices of the type of a fine needle.

The invention claimed is:

1. A process for the production of a biocompatible crosslinked polydensified monophasic gel, consisting of successive steps of:
   (a) starting a crosslinking reaction of a predetermined quantity of at least one biocompatible polymer in solution by the addition of a quantity of crosslinking agent in a first volume of a reaction mixture,
   (b) crosslinking said quantity of polymer,
   (c) adding a supplemental quantity of polymer of a molecular weight higher than 500,000 Da in solution with dilution of the reaction mixture so as to decrease an overall concentration of the polymer in a second volume of the reaction mixture,
   (d) continuing crosslinking in the second volume of the reaction mixture, and
   (e) stopping the crosslinking reaction by elimination of the crosslinking agent, to produce the polydensified monophasic gel.

2. The process according to claim 1, wherein the step of starting a crosslinking reaction is carried out in a basic pH medium.

3. The process according to claim 1, wherein the step of starting a crosslinking reaction is carried out in an acidic pH medium.

4. The process according to claim 1, wherein the step of stopping the crosslinking reaction is carried out by dialysis.

5. The process according to claim 1, wherein the polymers are of natural origin.

6. The process according to claim 5, wherein the polymers of natural origin are compounds selected from the group consisting of: hyaluronic acid, chondroitin sulfate, keratan, keratan sulfate, heparin, heparin sulfate, cellulose and its derivatives, alginates, xanthane, carrageenan, proteins or nucleic acids.

7. The process according to claim 5, wherein at least one of the polymers of natural origin is a polymer not naturally present in the human body, selected from the group consisting of: cellulose and its derivatives, alginates, xanthane, carrageenan, and a polymer which is crosslinked with at least one polymer naturally present in the human body selected from the group consisting of: hyaluronic acid, chondroitin sulfate, keratan, keratan sulfate, heparin, heparin sulfate, proteins or nucleic acids.

8. The process according to claim 1, wherein the crosslinking agent is a bifunctional or polyfunctional molecule comprising components selected from the group consisting of epoxys, epihalohydrins and divinylsulfone.

9. The process according to claim 2, wherein the step of stopping the crosslinking reaction is carried out by dialysis.

10. The process according to claim 3, wherein the step of stopping the crosslinking reaction is carried out by dialysis.

11. The process according to claim 1, wherein the step of stopping the crosslinking is carried out by dialysis.

12. The process according to claim 2, wherein the polymers are of natural origin.

13. The process according to claim 3, wherein the polymers are of natural origin.

14. The process according to claim 1, wherein the polymers are of natural origin.

15. The process according to claim 1, wherein the supplemental quantity of polymer is added in step c) in an amount of 10% of the predetermined quantity in step a).

16. A biocompatible crosslinked polydensified monophasic gel prepared by the process according to claim 1.

17. The gel according to claim 16, comprising at least one active ingredient dispersed therein.

18. The gel according to claim 16, wherein the degree of crosslinkage varies, and comprising crosslinked hubs interconnected by gel having a quantity of crosslinkage that progressively decreases from that of the hubs.

19. The gel according to claim 18, wherein the crosslinked hubs have a quantity of crosslinkage of about 25%, and the quantity of crosslinkage of the gel interconnecting the crosslinked hubs progressively decreases to about 1%.

20. A method to separate, replace or fill a biological tissue or increase the volume of said tissue or to supplement or replace a biological fluid comprising injecting the gel according to claim 16 in said tissue.

21. A process for the production of a biocompatible crosslinked polydensified monophasic gel, consisting of successive steps of:
  (a) starting a crosslinking reaction of a predetermined quantity of at least one biocompatible polymer in solution by the addition of a quantity of crosslinking agent in a first volume of a reaction mixture,
  (b) crosslinking said quantity of polymer,
  (c) adding a supplemental quantity of crosslinking agent,
  (d) adding a supplemental quantity of polymer of a molecular weight higher than 500,000 Da in solution with dilution of the reaction mixture so as to decrease an overall concentration of the polymer in a second volume of the reaction mixture,
  (e) continuing crosslinking in the second volume of the reaction mixture, and
  (f) stopping the crosslinking reaction by elimination of the crosslinking agent, to produce the polydensified monophasic gel.

22. The process according to claim 21, wherein the supplemental quantity of crosslinking agent is added during the step of adding a supplemental quantity of polymer.

23. A biocompatible crosslinked polydensified monophasic gel prepared by the process according to claim 21.

* * * * *